(12) United States Patent
Gong et al.

(10) Patent No.: US 10,197,476 B2
(45) Date of Patent: Feb. 5, 2019

(54) AUTOMATIC SLICING AND COLLECTING DEVICE AND METHOD FOR SLICING AND COLLECTING USING THE DEVICE

(71) Applicant: HUAZHONG UNIVERSITY OF SCIENCE AND TECHNOLOGY, Wuhan (CN)

(72) Inventors: Hui Gong, Wuhan (CN); Jing Yuan, Wuhan (CN); Tao Jiang, Wuhan (CN); Lei Deng, Wuhan (CN); Qingming Luo, Wuhan (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 0 days.

(21) Appl. No.: 15/691,698

(22) Filed: Aug. 30, 2017

(65) Prior Publication Data
US 2017/0363519 A1    Dec. 21, 2017

Related U.S. Application Data

(63) Continuation-in-part of application No. PCT/CN2017/077159, filed on Mar. 18, 2017.

(30) Foreign Application Priority Data

May 6, 2016   (CN) .......................... 2016 1 0296722

(51) Int. Cl.
*G01N 1/06* (2006.01)
*G01N 1/18* (2006.01)
(Continued)

(52) U.S. Cl.
CPC ................. *G01N 1/06* (2013.01); *G01N 1/18* (2013.01); *G01N 1/14* (2013.01); *G01N 35/1081* (2013.01);
(Continued)

(58) Field of Classification Search
CPC . Y10T 83/04; Y10T 83/0443; Y10T 83/0453; Y10T 83/2066; Y10T 83/929;
(Continued)

(56) References Cited

U.S. PATENT DOCUMENTS 4,363,783 A  *  12/1982  Sitte .......................... G01N 1/31
                                                              422/536
5,974,811 A  *  11/1999  Heid .......................... A61L 9/04
                                                              62/320

(Continued)

*Primary Examiner* — Phong Nguyen
(74) *Attorney, Agent, or Firm* — Matthias Scholl P.C.; Matthias Scholl

(57) ABSTRACT

An automatic slicing and collecting device, the device including: a first tank, a vibrating microtome, a first pipeline, and a second pipeline. The first tank is filled with a buffer solution. The vibrating microtome is disposed in the first tank. One end of the first pipeline is connected to the vibrating microtome to collect sections, and the other end of the first pipeline is connected to a pump. The pump includes a reversible motor. The first pipeline is provided with a first valve, and a filter is disposed between the pump and the first pipeline. One end of the second pipeline is disposed between the first valve of the first pipeline and the pump, and the second pipeline is provided with a second valve.

18 Claims, 4 Drawing Sheets

(51) Int. Cl.
*G01N 1/14* (2006.01)
*G01N 35/10* (2006.01)

(52) U.S. Cl.
CPC . *G01N 2001/061* (2013.01); *G01N 2001/185* (2013.01); *Y10S 83/9155* (2013.01)

(58) Field of Classification Search
CPC ........ Y10S 83/9155; G01N 1/06; G01N 1/18; G01N 1/14; G01N 1/00; G01N 1/10; G01N 35/1081; G01N 2001/061; G01N 2001/185; G01N 2001/002; G01N 2001/1006; G01N 2001/1012; G01N 2001/1025
See application file for complete search history.

(56) References Cited

U.S. PATENT DOCUMENTS

2006/0086221 A1* 4/2006 Kong ................. G01N 1/06 83/401
2013/0019725 A1* 1/2013 Magavi .............. G01N 1/06 83/24

* cited by examiner

AUTOMATIC SLICING AND COLLECTING DEVICE AND METHOD FOR SLICING AND COLLECTING USING THE DEVICE

CROSS-REFERENCE TO RELATED APPLICATIONS

This application is a continuation-in-part of International Patent Application No. PCT/CN2017/077159 with an international filing date of Mar. 18, 2017, designating the United States, now pending, and further claims foreign priority to Chinese Patent Application No. 201610296722.5 filed May 6, 2016. The contents of all of the aforementioned applications, including any intervening amendments thereto, are incorporated herein by reference.

BACKGROUND OF THE INVENTION

Field of the Invention

The invention relates to an automatic slicing and collecting device and a method for slicing and collecting using the device.

Description of the Related Art

In modern biological research and medical examination, vibrating microtomes are usually used to slice biological tissues into thin sections. Conventionally, the sections are picked and collected manually, which is inefficient and laborious.

In recent years, automatic slicing and collecting devices have been developed. The devices collect the thin sections using water channels. However, because a plurality of water channels and controllers is required, the devices are complex and expensive to produce.

SUMMARY OF THE INVENTION

In view of the above-described problems, it is one objective of the invention to provide an automatic slicing and collecting device and a method for slicing and collecting using the device. By using the device, sections sliced by the vibrating microtome are automatically collected, improving the slicing and collecting efficiency.

To achieve the above objective, in accordance with one embodiment of the invention, there is provided an automatic slicing and collecting device, comprising: a first tank, a vibrating microtome, a first pipeline, and a second pipeline. The first tank is filled with a buffer solution. The vibrating microtome is disposed in the first tank. One end of the first pipeline is connected to the vibrating microtome to collect sections, and the other end of the first pipeline is connected to a pump. The pump comprises a reversible motor. The first pipeline is provided with a first valve, and a filter is disposed between the pump and the first pipeline. One end of the second pipeline is disposed between a first valve of the first pipeline and the pump, and the second pipeline is provided with a second valve.

In a class of this embodiment, the other end of the second pipeline is provided with a dispenser head. A perforated plate is disposed below the dispenser head.

In a class of this embodiment, an annular sieve is sleeved on the dispenser head, and a diameter of the annular sieve equals to a diameter of pores on the perforated plate.

In a class of this embodiment, the vibrating microtome comprises a blade and a blade clamp. The blade is clamped by the blade clamp. The blade clamp is provided with a through hole. The through hole is hollow. One end of the through hole faces toward the blade, and the other end of the through hole communicates with the first pipeline.

In a class of this embodiment, the device further comprises a three-axis manipulator. The first valve, the second valve, and the dispenser head are disposed on the three-axis manipulator, respectively.

In a class of this embodiment, the pump communicates with the first tank via a third pipeline.

In a class of this embodiment, the device further comprises a collecting tank. The perforated plate is disposed in the collecting tank. The collecting tank communicates with the first tank via a fourth pipeline.

In accordance with another embodiment of the invention, there is provided a method for slicing and collecting using the device, the method comprising:

1) closing the second valve; opening the first valve; controlling the reversible motor to rotate to drive sections sliced by the vibrating microtome to flow to the first pipeline along with the buffer solution;
2) opening the second valve; closing the first valve; controlling the reversible motor to rotate reversely to drive the sections in the first pipeline to flow to a dispenser head via a second pipeline along with the buffer solution;
3) controlling a three-axis manipulator to drive the dispenser head to align with a pore on a perforated plate and releasing the sections to the pore; and
4) repeating 1)-3) to perform automatic slicing and collecting until the sections are dispensed in each pore of the perforated plate.

In a class of this embodiment, an annular sieve is disposed on the dispenser head to prevent overflow of the sections from the pore of the perforated plate; and the buffer solution overflowed from the pore is collected by a collecting tank and is returned to the first tank via a fourth pipeline.

In a class of this embodiment, when the reversible motor rotates forward, the buffer solution is pumped back to the first tank via a third pipeline.

Advantages of the device and the method according to embodiments of the invention are summarized as follows:

1. By using the device, the sample sections are automatically collected from the vibrating microtome, and without manual collection, the working efficiency is improved.
2. The automatic slicing and collecting device is easy to assemble and operate, and the method for slicing and collecting using the device is highly efficient.

BRIEF DESCRIPTION OF THE DRAWINGS

The invention is described hereinbelow with reference to the accompanying drawings, in which.

Figure 1:
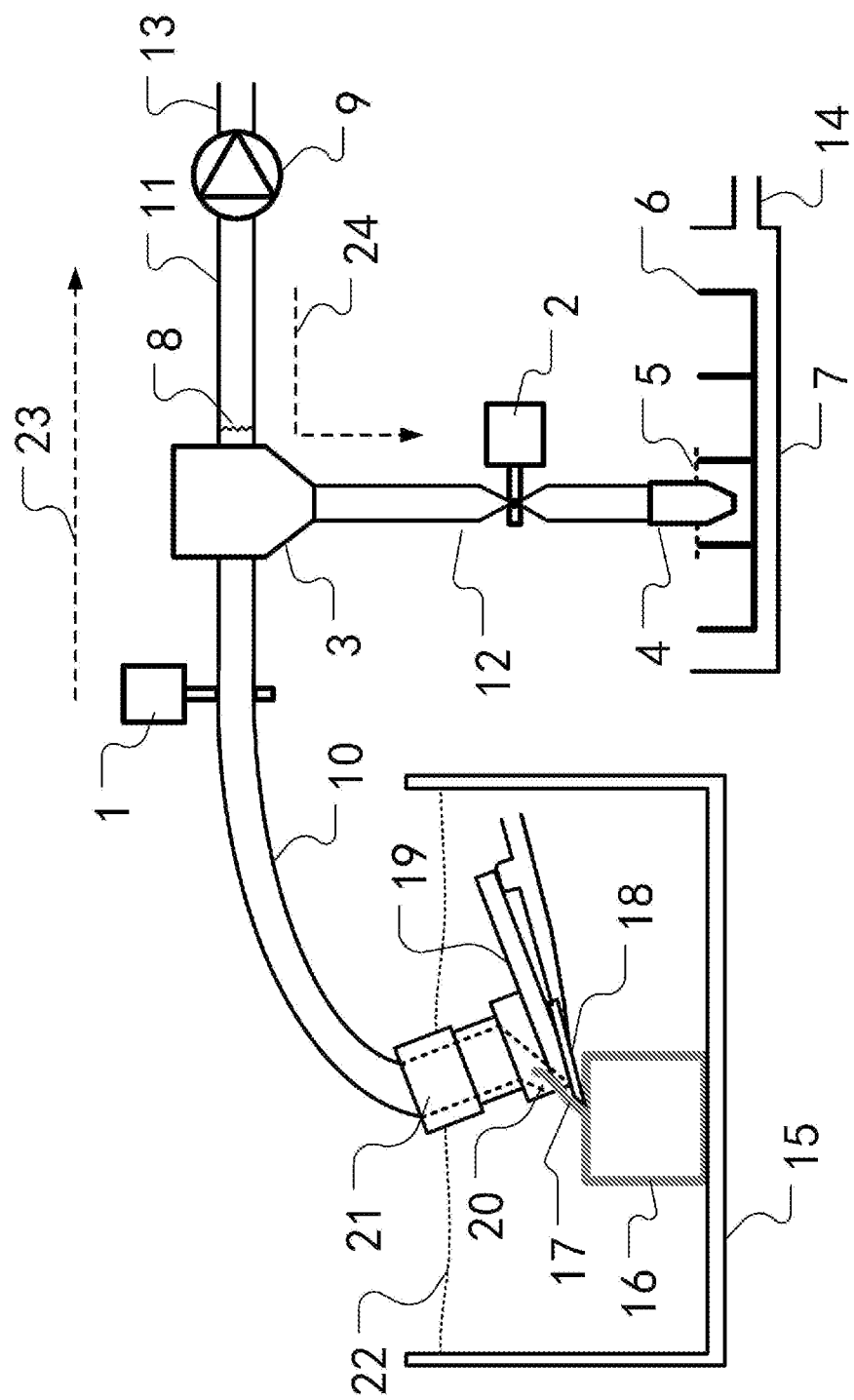
FIG. 1 is a schematic diagram of an automatic slicing and collecting device in accordance with one embodiment of the invention.

In the drawings, the following reference numbers are used: 1. First valve; 2. Second valve; 3. Three-way section storage; 4. Dispenser head; 5. Annular sieve; 6. Perforated plate; 7. Collecting tank; 8. Filter; 9. Pump; 10. First pipeline; 11. Second pipeline; 12. Third pipeline; 13. Fourth pipeline; 14. Fifth pipeline; 15. First tank; 16. Biological sample; 17. Sections; 18. Blade; 19. Blade clamp; 20. Through hole; 21. Upper end of through hole; 22. Buffer solution; 23. Flow direction of buffer solution when reversible motor is rotated forward; 24. Flow direction of buffer solution when reversible motor rotate reversely; 25. First screw hole; 26. Second screw hole; 27. Expandable end of through hole; and 28. Three-axis manipulator.

DETAILED DESCRIPTION OF THE EMBODIMENTS

For further illustrating the invention, experiments detailing an automatic slicing and collecting device and a method for slicing and collecting using the device are described below.

Figure 2:
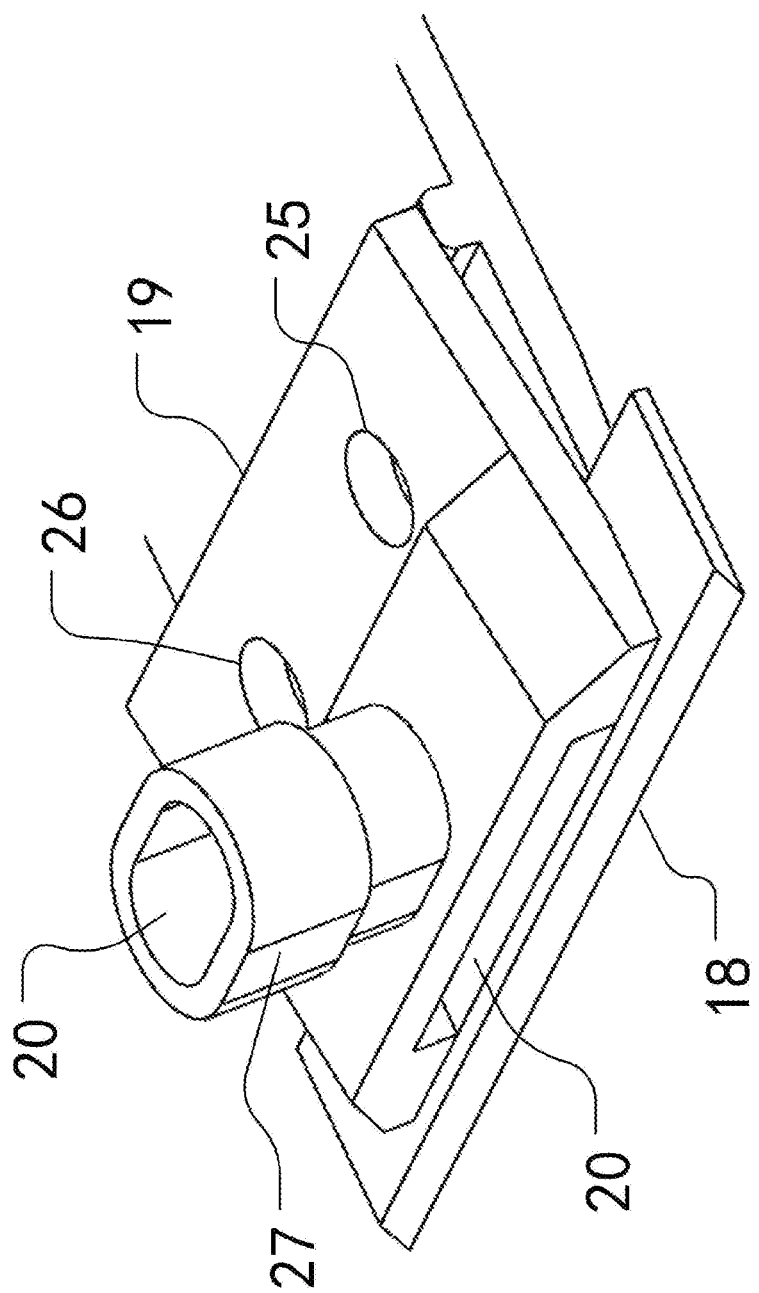
FIG. 2 is a three-dimensional schematic diagram of an automatic slicing and collecting device in accordance with one embodiment of the invention.

FIG. 1 is a schematic diagram of an automatic slicing and collecting device. The device comprises a first tank 15, and the first tank 15 is filled with a buffer solution 22. Biological sample 16 and a vibrating microtome are disposed in the buffer solution 22, and the slicing process is conducted in liquid. As shown in FIG. 2, the vibrating microtome comprises a blade 18 and a blade clamp 19. The blade is clamped by the blade clamp 19. Screw nuts are screwed in the first screw hole 25 and the second screw hole 26, respectively, so as to fix the blade 18. The blade clamp 19 is provided with a through hole 20. A lower end of the through hole 20 faces toward the blade 18.

The automatic slicing and collecting device further comprises a three-way section storage 3, a first pipeline 10, a second pipeline 11, a third pipeline 12, a fourth pipeline 13, a fifth pipeline 14, and a perforated plate 6.

One end of the first pipeline 10 is connected to a first channel of the three-way section storage 3, and the other end of the first pipeline is connected to an upper end of the through hole 20. One side of the through hole 20 is provided with an expandable end 27. The expandable end 27 is configured to facilitate the fixed connection with the first pipeline 10. The first pipeline 10 is provided with a first valve 1, and the first valve 1 is configured to control on-off of the first pipeline 10. Optionally, the first valve 1 is an electromagnetic pinch valve.

One end of the third pipeline 12 is connected to a second channel of the three-way section storage 3, and the other end of the third pipeline is connected to a dispenser head 4. A perforated plate 6 is disposed below the dispenser head 4. An annular sieve 5 is sleeved on the dispenser head 4, and a diameter of the annular sieve 5 equals to a diameter of pores on the perforated plate 6. When the dispenser head 4 is inserted to each pore on the perforated plate 6, the annular sieve 5 contacts with the inner wall of each pore. The third pipeline is provided with a second valve 2, and the second valve 2 is configured to control on-off of the third pipeline 12. Optionally, the second valve 2 is an electromagnetic pinch valve. The perforated plate 6 is disposed in a collecting tank 7. The collecting tank 7 communicates with the first tank 15 via a fifth pipeline 14.

One end of the second pipeline 11 is connected to a third channel of the three-way section storage 3, and a joint between the second pipeline and the third channel is provided with a filter 8. The other end of the second pipeline is connected to a pump 9. The pump comprises a reversible motor. The pump 9 communicates with the first tank 15 via a fourth pipeline 13.

Figure 3:
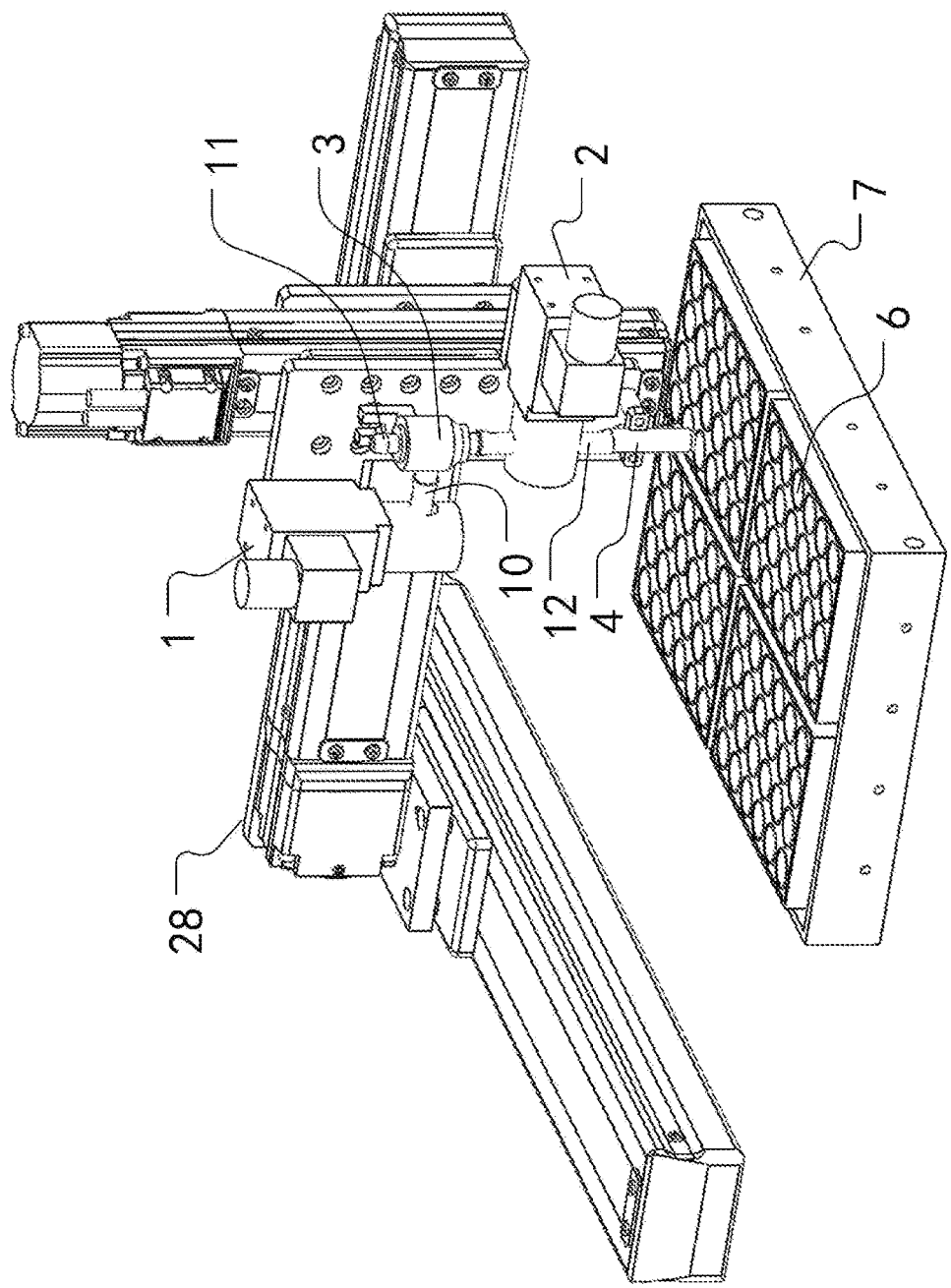
FIG. 3 is a schematic diagram of a vibrating microtome in accordance with one embodiment of the invention.

To ensure an automatic, fast, and continuous collection of the sections, the automatic slicing and collecting device further comprises a three-axis manipulator 28. The first valve 1, the second valve 2, the three-way section storage 3, and the dispenser head 4 are disposed on the three-axis manipulator 28, respectively, as shown in FIG. 3.

The parts of the automatic slicing and collecting device are illustrated as follows: the first valve 1 and the second valve 2 are electromagnetic pinch valve. The three-way section storage 3 and the dispenser head 4 are plastic workpieces. The annular sieve 5 and the filter 8 are processed from stainless steel filter. The perforated plate 6 is a 24-well plate made from polystyrene. The collecting tank 7 and the first tank 15 are aluminum workpieces. The pump 9 is a gear pump driven by a brushless DC motor, and configured to adjust the current to flow at between 50 and 1000 mL/min. The first pipeline 10, the second pipeline 11, the third pipeline 12, the fourth pipeline 13, and the fifth pipeline 14 are silicon tubes. An inner diameter of the silicon tubes is 6.4 mm, and an outer diameter of the silicon tubes is 9 mm. The blade 18 uses zirconia blade from Electron Microscopy Sciences. The blade clamp 19 is a stainless steel workpiece. The three-axis manipulator 28 is the three-axis manipulator T6L-T5L-T4L from Yamaha Corporation.

Figure 4:
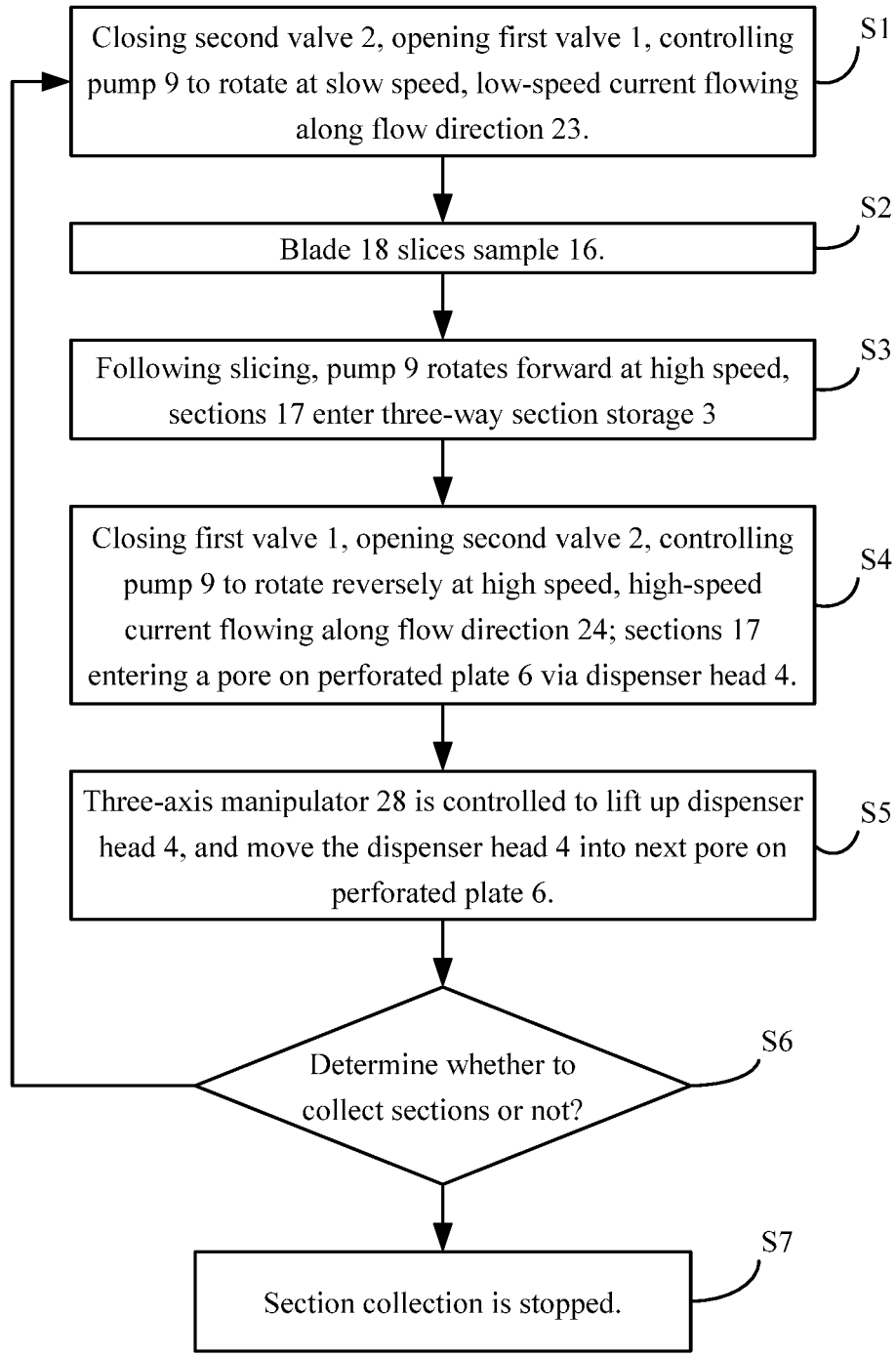
FIG. 4 is a flow chart of a method for slicing and collecting using an automatic slicing and collecting device in accordance with one embodiment of the invention.

FIG. 4 is a flow chart showing automatic section collection using an automatic slicing and collecting device. The working process of the device is illustrated as follows:

S1: The second valve 2 is closed, and the first valve 1 is opened. The pump 9 is controlled to rotate at slow speed to form a low-speed stable current flowing along the flow direction 23 of buffer solution when the reversible motor is rotated forward. The buffer solution 22 enters the through hole via an inlet at a lower end of the through hole 20. The buffer solution flows through the upper end of the through hole 20, the first pipeline 10, the three-way section storage 3, the filter 8, the second pipeline 11, and the pump 9, and the buffer solution returns back to the first tank 15 via the fourth pipeline 13.

S2: Driven by the vibrating microtome, the blade 18 starts to slice the biological sample 16. Sections 17 produced by the vibrating microtome is pushed by the low-speed stable current flowing along the flow direction 23 of buffer solution, and enters the through hole from the inlet at the lower end of the through hole 20. The current is at low speed so as to avoid tear of the sections 17.

S3: When the slicing of the biological sample 16 using the blade 18 is completed, the pump 9 increases rotation speed to form a high-speed stable current flowing along the flow direction 23 of buffer solution when the reversible motor is rotated forward. The sections 17 are pushed by the current to the three-way section storage 3 via the first pipeline 10. The filter 8 is configured to stop the sections 17 from entering the second pipeline 11 via the three-way section storage 3.

S4: The first valve 1 is closed. The second valve 2 is opened. The reversible motor of the pump 9 is controlled to rotate reversely to form a high-speed stable current of the buffer solution flowing along the flow direction 24. The buffer solution from the first tank 15 flows through the fourth pipeline 13, the pump 9, the second pipeline 11, the filter 8, the three-way section storage 3, the third pipeline 12, and the dispenser head 4 to a pore on the perforated plate 6. The sections 17 are pushed by the high-speed current flowing along the flow direction 24, and are transmitted from the three-way section storage 3, through the third pipeline 12 and the dispenser head 4, to a pore on the perforated plate 6. The annular sieve 5 on the dispenser head 4 is configured to prevent overflow of the sections 17 from the pore of the perforated plate 6. Overflowed buffer solution is collected by the collecting tank 7 and is returned to the first tank 15 via the fifth pipeline 14.

S5: The three-axis manipulator 28 is controlled to lift up the dispenser head 4, and move the dispenser head 4 into next pore on the perforated plate 6. The annular sieve 5 on the dispenser head 4 contacts with the inner wall of pores.

S6: Determine whether to continue section collection or not. If the section collection is continued, S1-S5 are repeated until the section collection is completed. If the section collection is completed, move to next step.

S7: Section collection is stopped.

To automate the section collection, the first valve 1, the second valve 2, the pump 9, and the three-axis manipulator 28 are controlled using industrial control computers. Using the industrial control computers to automate the electrical devices belongs to the prior art, and no need to illustrate herein.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An automatic slicing and collecting device, the device comprising:
   a first tank;
   a vibrating microtome for slicing a biological sample into sections;
   a first pipeline;
   a second pipeline;
   a third pipeline; and
   a three-way section storage;
   wherein
   the first tank is filled with a buffer solution;
   the vibrating microtome is disposed in the first tank;
   one end of the first pipeline is connected to the vibrating microtome, and the other end of the first pipeline is connected to the three-way section storage;
   one end of the second pipeline is connected to the three-way section storage, and the other end is connected to a pump comprising a reversible motor;
   the first pipeline is provided with a first valve, and a filter is disposed between the pump and the three-way section storage to stop the sections entering the second pipeline; and
   one end of the third pipeline is connected to the three-way section storage, and the second pipeline is provided with a second valve.

2. The device of claim 1, wherein the other end of the third pipeline is provided with a dispenser head; and a perforated plate is disposed below the dispenser head.

3. The device of claim 2, wherein an annular sieve is sleeved on the dispenser head, and a diameter of the annular sieve equals to a diameter of pores on the perforated plate.

4. The device of claim 3, wherein the vibrating microtome comprises a blade and a blade clamp; the blade is clamped by the blade clamp; the blade clamp is provided with a through hole; the through hole is hollow; one end of the through hole faces toward the blade, and the other end of the through hole communicates with the first pipeline.

5. The device of claim 4, wherein the device further comprises a three-axis manipulator; and the first valve, the second valve, the three-ways section storage, and the dispenser head are disposed on the three-axis manipulator, respectively.

6. The device of claim 5, wherein the pump communicates with the first tank via the first pipeline, the three-way section storage, and the first valve.

7. The device of claim 6, wherein the device further comprises a collecting tank; the perforated plate is disposed in the collecting tank; and the collecting tank communicates with the first tank via a fourth pipeline.

8. The device of claim 2, wherein the vibrating microtome comprises a blade and a blade clamp; the blade is clamped by the blade clamp; the blade clamp is provided with a through hole; the through hole is hollow; one end of the through hole faces toward the blade, and the other end of the through hole communicates with the first pipeline.

9. The device of claim 8, wherein the device further comprises a three-axis manipulator; and the first valve, the second valve, the three-ways section storage, and the dispenser head are disposed on the three-axis manipulator, respectively.

10. The device of claim 9, wherein the pump communicates with the first tank via the first pipeline, the three-way section storage, and the first valve.

11. The device of claim 10, wherein the device further comprises a collecting tank; the perforated plate is disposed in the collecting tank; and the collecting tank communicates with the first tank via a fourth pipeline.

12. The device of claim 1, wherein the vibrating microtome comprises a blade and a blade clamp; the blade is clamped by the blade clamp; the blade clamp is provided with a through hole; one end of the through hole faces toward the blade, and the other end of the through hole communicates with the first pipeline.

13. The device of claim 12, wherein the device further comprises a three-axis manipulator; and the first valve, the second valve, the three-ways section storage, and a dispenser head are disposed on the three-axis manipulator, respectively.

14. The device of claim 13, wherein the pump communicates with the first tank via the first pipeline, the three-way section storage, and the first valve.

15. The device of claim 14, wherein the device further comprises a collecting tank; a perforated plate is disposed in the collecting tank; and the collecting tank communicates with the first tank via a fourth pipeline.

16. A method for slicing and collecting using the device of claim 1, the method comprising:
   1) closing the second valve; opening the first valve; controlling the reversible motor to rotate to drive sections sliced by the vibrating microtome to flow to the first pipeline along with the buffer solution;
   2) opening the second valve; closing the first valve; controlling the reversible motor to rotate reversely to drive the sections in the first pipeline to flow to a dispenser head via the third pipeline along with the buffer solution;
   3) controlling a three-axis manipulator to drive the dispenser head to align with a pore on a perforated plate and releasing the sections to the pore; and
   4) repeating steps 1-3 to perform automatic slicing and collecting until the sections are dispensed in each pore of the perforated plate.

17. The method of claim 16, wherein an annular sieve is disposed on the dispenser head to prevent overflow of the sections from the pore of the perforated plate;

and the buffer solution overflowed from the pore is collected by a collecting tank and is returned to the first tank via a fifth pipeline.

18. The method of claim 17, wherein the reversible motor, further communicates to the first tank via a fourth pipeline.

* * * * *